United States Patent [19]

Wells

[11] 4,443,345

[45] Apr. 17, 1984

[54] SERUM PREPARATOR

[76] Inventor: John R. Wells, 4372 Keystone Ave., Culver City, Calif. 90230

[21] Appl. No.: 393,037

[22] Filed: Jun. 28, 1982

[51] Int. Cl.$^3$ ............................................. B01D 21/26
[52] U.S. Cl. ..................................... 210/782; 210/789; 210/359; 210/516; 210/927; 422/101; 604/403; 215/308
[58] Field of Search ............... 210/514, 515, 516, 517, 210/518, 359, 782, 927, DIG. 24, 789, 190, 231; 604/403, 406; 422/101; 251/297; 215/308, 311, 355, 364; 220/307

[56] References Cited

U.S. PATENT DOCUMENTS

| | | | |
|---|---|---|---|
| 3,094,308 | 6/1903 | Conrad | 251/297 |
| 3,355,142 | 11/1967 | Kammerer, Jr. et al. | 251/297 |
| 3,814,248 | 6/1974 | Lawhead | 210/516 |
| 3,891,553 | 6/1975 | Ayres | 210/516 |
| 3,901,402 | 8/1975 | Ayres | 210/516 |
| 3,931,010 | 1/1976 | Ayres et al. | 210/516 |
| 3,945,928 | 3/1976 | Ayres | 210/927 |
| 4,057,499 | 11/1977 | Buono | 210/516 |
| 4,202,769 | 5/1980 | Greenspan | 210/516 |

*Primary Examiner*—Benoît Castel
*Assistant Examiner*—John W. Czaja
*Attorney, Agent, or Firm*—Donald G. Lewis

[57] ABSTRACT

The invention is a device and a method for preparing serum from blood. The invention is used in conjunction with the centrifugal separation of serum from blood for filtering fibrin and other particulates from the separated serum and for partitioning the serum filtrate from unfiltered blood. During the first phase of centrifugation, a detent holds the serum preparator in check within the centripedal end of a tube containing the blood while the components of blood separate by sedimentation and backflow. Once all cellular components have sedimented to the pellet, the second phase of centrifugation begins and the sedimentation of the serum preparator is initiated by a triggering centrifugal force. During sedimentation, the serum preparator forces displaced serum to pass across a filter spanning an aperture through the serum preparator. The sedimentation velocity of the device and the rate of filtration are controlled by a brake on the serum preparator. The serum preparator is a density device which is approximately isopycnic with normal whole blood. The density of the serum preparator causes it to seek an isopycnic equilibrium stop position near the interface of the separated serous and cellular components. At the isopycnic stop position, the serum preparator forms an impermeable barrier to protect the serum filtrate from contamination by the cellular component during storage and decanting.

16 Claims, 12 Drawing Figures

SERUM PREPARATOR

BACKGROUND OF THE INVENTION

The invention relates to the preparation of serum for clinical analysis. The invention is a device and method used for separating serum from blood by centrifugation, for filtering the separated serum, and for isolating the serum filtrate from the unfiltered portion during storage and decanting.

The invention is a serum preparator used in the preparation of serum for analysis. The serum preparator is a device which filters and partitions serum in conjunction with the centrifugal separation of the cellular and serous components of blood. The serum preparator restrains the initiation and rate of filtration of serum to enable complete centrifugal separation and to optimize the filtration rate. The serum preparator is an isopycnic device which sediments under centrifugation to its equilibrium position within the interface of the separated cellular and serous components and partitions the serum filtrate from the unfiltered components.

Serum is formed when blood is allowed to clot and to separate into its cellular and serous components. The separation of cellular and serous components can be accelerated by centrifugation in a centrifuge tube. During centrifugation, the cellular components sediment to form a cellular pellet and the serum backflows to form a clarified supernatant. The cellular component comprises both clotted blood cells and uncoagulated blood cells. The clot comprises the major cellular component of well clotted blood. The clot sediments quickly. Uncoagulated cells comprise a minor cellular component of well clotted blood. Uncoagulated cells sediment relatively slowly. Separation is complete only after the slowly sedimenting uncoagulated cells have pelleted. Prior art devices similar to the serum preparator have failed to reckon with the slow sedimentation of the minor component of uncoagulated cells. Incomplete separation of the serum results in the contamination of the serum filtrate and compromises the diagnostic utility of the serum analysis.

If the serum is to be processed by an automatic serum analyzer, it should first be filtered to remove fibrin. Fibrin in the serum can cause an automatic serum analyzer to clog. The rate of filtration should be controlled in order to prevent blowby around the filter and to optimize the efficiency of filtration.

To prevent contamination of the serum filtrate during storage and decanting from the tube, the serum filtrate should be partitioned from the cellular pellet. Partitioning is needed to prevent the contamination of the serum filtrate by the diffusion of products from the metabolically active cellular pellet. Such contamination can cause the serum assay to reflect an erroneous level of metabolites, different than the level in the patient's circulation. Also, partitioning is needed to prevent contamination by the cellular pellet during decanting.

Several partition devices are known which are used in conjunction with the centrifugal separation of the components of blood. Such devices are simple barriers which are inserted and travel within a centrifuge tube and which are driven by centrifugal force until they are stopped at the interface by the isopycnic equilibrium of the device. Examples of such devices are disclosed in U.S. Pat. No. 3,508,653 (Coleman) and U.S. Pat. No. 4,001,122 (Griffin). However, these partition devices are unrestrained and sediment simultaneously with the cellular components. These partition devices can overtake and capture the slowly sedimenting uncoagulated cells. This results in the contamination and incomplete separation of the serum.

A partition device which includes means to restrain the initiation of sedimentation is known. The device is disclosed in U.S. Pat. No. 3,972,812 (Gresl). This device comprises a disc of partition material with a substantial void volume. The disc floats atop the samle blood until the void volume fills with fluid, after which the device begins to sediment until it reaches its isopycnic equilibrium. At the isopycnic equilibrium within the interface, the device acts to partition the separated components. The time required for filling the void volume causes sufficient delay for uncoagulated cells to sediment to the cellular pellet ahead of the partition device. However, this device does not teach how to combine a filter device with the partition device.

Devices which combine the filtration and partitioning of serum in conjunction with the centrifugal separation of serum are known. Examples of such devices are disclosed in U.S. Pat. No. 3,931,018 (North) and U.S. Pat. No. 4,202,769 (Greenspan). These devices filter and partition serum in conjunction with the centrifugal separation of the components of blood. However, neither of these devices have means to restrain the initiation of sedimentation or to control the rate of filtration. These devices overtake and capture or lysis the slowly sedimenting uncoagulated cells. Capture causes contamination by incomplete separation. Lysis causes contamination by the lysate. The uncontrolled rate of filtration can cause filter overload and blowby.

A combination filtration and partition device which includes means for restraining the initiation of sedimentation is known. This device is disclosed in U.S. Pat. No. 3,931,010 (Ayres). This device includes a valve which acts as a means for restraining the initiation of sedimentation of the device. The valve in this device is closed at low centrifugation speeds and open at higher speeds. The device sediments only when the valve is open. This enables the separation step to occur prior to the filtration step. The separation step occurs at a low centrifuge speeds with the valve closed and the filtration step occurs at a higher centrifuge speeds with the valve open. However, this device is not an isopycnic device. This device teaches that a mechanical stop is required to stop the sedimentation of such a combination device. Because the position of the mechanical stop is fixed in manufacture, the device is unable to accommodate the separation of blood samples with divergent hematocrits or with divergent sample volumes. The hematocrit of pathological samples of blood can range from 20% to 70%. Serum filtrate from samples with a high hematocrit can be contaminated with cellular material; serum filtrate from samples with a low hematocrit can result in the loss of usable serum. The volume of blood sample to be prepared must be correlated with the position of the mechanical stop. For instance, the preparation of a small volume of blood sample from an infant would require a small sized device. Also, the Ayres device lacks means to restrain the sedimentation velocity of the device and the rate of filtration in order to avoid filter blowby and overload.

SUMMARY OF THE INVENTION

The invention is a serum preparator and a method for preparing a serum sample for analysis. The purpose of the invention is to facilitate the process of serum preparation and to enhance the quality of the serum preparation.

The serum preparator is to be used in conjunction with the centrifugal separation of a sample of blood contained within a centrifuge tube. The serum separator is a piston device which is inserted into the tube and is restrained within the tube while the blood is centrifugally separated into its serous and cellular components. After separation, the serum preparator is triggered to filter the separated serum by sedimenting through the serum and by forcing the serum in its path to pass through a filter. The serum preparator proceeds to sediment to its isopycnic equilibrium position within the interface between the separated serous and cellular components. When the serum preparator comes to rest, it forms a partition between the filtered serum and unfiltered components.

An important component of the invention is the recognition of the problem which it solves, viz. the invention eliminates the contamination of the serum filtrate by cellular components, particularly the slowly sedimenting uncoagulated cells which comprise a minor cellular component.

The serum preparator restrains its own sedimentation during the centrifugal separation of the serous and cellular components of the blood sample. This self restraint enables all cellular components of blood to sediment to the pellet without being overtaken by the serum preparator. This prevents the cellular blowby, capture, and lysis which typically results from the simultaneous initiation of sedimentation of both the serum preparator and the sample components. Cellular blowby, capture, and lysis compromise the quality and utility of the serum preparation. The serum preparator includes a detent or a brake or both for restraining the sedimentation of the serum preparator during the separation phase.

After the separation phase, the serum preparator sediments down the centrifuge tube and filters the separated serum to remove fibrin and other particulates from the serum. The rate of sedimentation and thereby the rate of filtration is controlled by a brake on the serum preparator. The brake may be frictional or hydraulic or both. A frictional brake reduces both the differential pressure across the filter and the rate of flow across the filter. A hydraulic brake reduces only the rate of flow across the filter. Reducing the rate of flow across the filter reduces filter overload. Reducing the differential pressure across the filter, reduces filter blowby. To further reduce filter blowby, serum preparator has a piston with an annular seal in contact with the tube wall and locates the filter across an aperture which passes through the piston and which guides the displaced serum during sedimentation. The piston holds the filter across the aperture in a manner which eliminates blowby around the filter. The serum preparator includes a brake, either hydraulic or frictional or both for restraining the rate of sedimentation of the serum preparator.

The filtration process stops after the serum preparator has passed through the separated serum and comes to rest at its isopycnic equilibrium at the interface of the separated serum and cellular components. The density of the serum preparator is chosen to be isopycnic to the overall density of normal whole blood, with a specific gravity between 1.01 and 1.085. The density of the serum supernatant is relatively less than the density of the cellular pellet. The isopycnic density of the serum preparator is intermediate to the densities of the separated serous and cellular components. Being more dense than the separated serum, the serum preparator sediments through the serum supernatant during centrifugation. The serum preparator continues to sediment until it enters and partially displaces the pellet formed by the heavier cellular component. The sedimentation of the serum preparator stops when it reaches its isopycnic equilibrium at the interface where the serum preparator "floats" partially submersed in the cellular phase and partially overlaid by the serum filtrate. The filtration process stops when the serum preparator ceases to sediment.

The brake on the serum preparator dampens the momentum of the serum preparator so that it will not overshoot its isopycnic equilibrium position (stop position). Overshooting its stop position and entering the cellular pellet can cause the serum preparator to capture cellular material. For this reason, the serum preparator includes a brake.

In order to decrease the sensitivity of the isopycnic equilibrium point to changes in the density of the whole blood or its components, the composition of the serum preparator is chosen so that the center of mass is displaced centrifugally from the center of volume, viz. the centrifugal end of the device is more dense than the centripetal end.

When the serum preparator stops sedimenting and reaches its isopycnic equilibrium position, it forms a partition to divide and to protect the serum filtrate from the unfiltered components. The partition prevents contamination of the serum filtrate during storage and decanting. The serum preparator includes a partition to guard the serum filtrate against contamination from either the diffusion of solutes (e.g. cellular metabolites) or the movement of blood cells. The partition guarding against cellular movement utilizes the combination of the piston itself, the annular seal, and the filter to comprise the partition. The cellular partition protects against contamination during decanting. However, solutes can diffuse across the filter. If long term storage is anticipated, the solute partition should be used. This species includes an impermeable partition barrier which stops the diffusion of solutes into the serum filtrate.

It is a purpose of this invention to provide the serum preparator with means for restraining the sedimentation of the piston in order to exclude slowly sedimenting particulates from the serum filtrate.

It is a purpose of this invention to provide the serum preparator with a detent for delaying the initiation of the sedimentation of the serum preparator during centrifugation. The detent holds the serum preparator in check and allows the cellular components sufficient time to sediment and to separate from the serum. This prevents the capture and lysis of uncoagulated cells by the serum preparator.

It is a purpose of this invention to provide the serum preparator with a brake for restraining the sedimentation velocity of the serum preparator. Braking the serum preparator decreases rate of flow across the filter, thereby decreasing the tendency for the filter to overload. A hydraulic brake suffices for this purpose. Braking the serum preparator with a frictional brake also decreases the differential pressure across the serum preparator, thereby decreasing the tendency for unfiltered serum to blow by the serum preparator. This improves the effectiveness of the filtration. Extreme braking can enable separation to preceed filtration and thereby impart some of the benefits of the use of the detent. However, use extreme braking will significantly lengthen the overall time course of serum preparation. Braking the serum preparator dampens its momentum so that it will not overshoot its isopycnic stop position.

It is a purpose of this invention to provide the serum preparator with a combination of different species of means for restraining the sedimentation of the piston, viz. a detent, a frictional brake, and a hydraulic brake.

It is a purpose of this invention to prevent blowby of unfiltered serum around the filter of the sedimenting serum preparator. Blowby is prevented by positioning the filter within an aperture through the serum preparator adapted for the passage of displaced serum and by tightly blocking all alternate pathways around the serum preparator and the filter.

It is a purpose of this invention to provide the serum preparator with a partition for preventing the contamination of the serum filtrate by cellular pellet material and from soluable metabolites from the pellet.

It is a purpose of this invention to displace the center of mass of the serum preparator from the center of volume in order to decrease the sensitivity of the isopycnic equilibrium point to changes in the density of the whole blood or its components.

BRIEF DESCRIPTION OF THE DRAWINGS

FIG. 9 shows the serum preparator inserted in a tube containing clotted blood, the serum preparator in its catch position supported by the lip of the tube, and showing the whole assembly prior to the application of any centrifugal force.

FIG. 10 shows the serum preparator after the application of a first centrifugal force but prior to the application of a triggering force with the serum preparator still in its catch position supported by the lip of the tube and shows the cellular component having been sedimented and the serum clarified as a supernatant.

FIG. 11 shows the serum preparator a short time after the application of the triggering force with the serum preparator having been activated by the triggering force and having traveled partially down the tube effecting a filtration of some of the serum.

FIG. 12 shows the serum preparator after the application of the triggering force but a short time prior to the removal of all centrifugal force with the serum preparator having traveled to its point of its isopycnic equilibrium within the interface of the cellular pellet and the clarified serum and having completed the filtration and partitioning of the clarified serum.

DESCRIPTION OF THE PREFERRED EMBODIMENT

Figure 1:
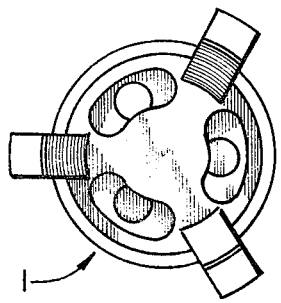
FIG. 1 is an orthographic view of a preferred embodiment of the serum preparator, showing the top of the serum preparator.
Figure 3:
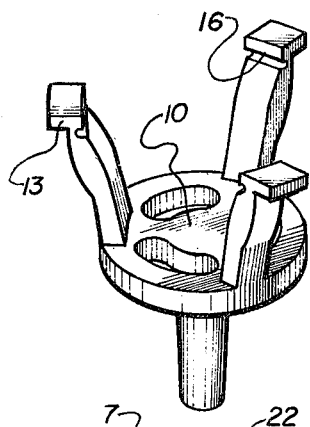
FIG. 3 is an exploded view in the same perspective as FIG. 2 of the serum preparator of FIG. 1, showing all the elements of the preferred embodiment.
Figure 6:
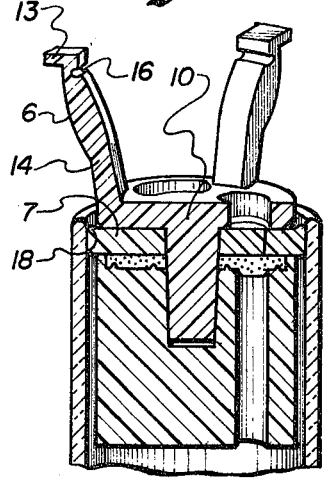
FIG. 6 is a sectional view of the serum preparator of FIG. 1 as the serum preparator is being inserted into a tube in preparation to use the serum preparator.
Figure 2:
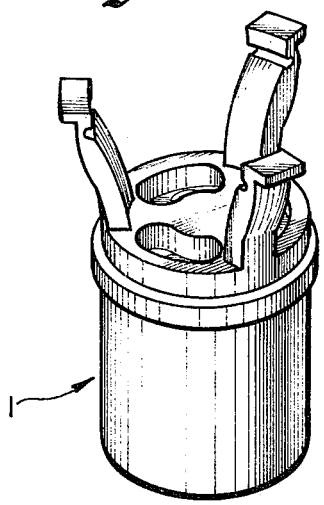
FIG. 2 is a view in perspective of the serum preparator of FIG. 1, showing the side of the serum preparator.
Figure 7:
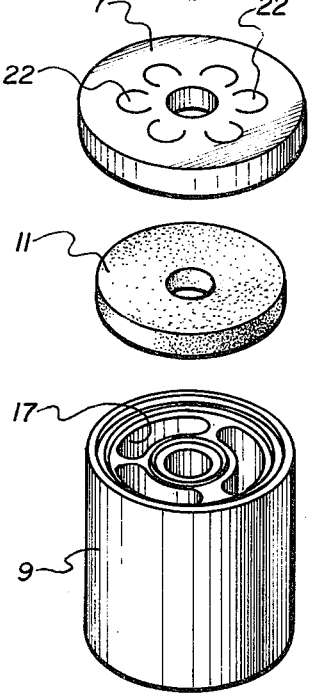
FIG. 7 is a sectional view of the serum preparator continued from FIG. 6, showing the serum preparator inserted into the tube and in its catch position with the catch of the detent resting on the lip of the tube, ready to hold the serum preparator in check when the tube is centrifuged to separate the blood into its components.
Figure 7:
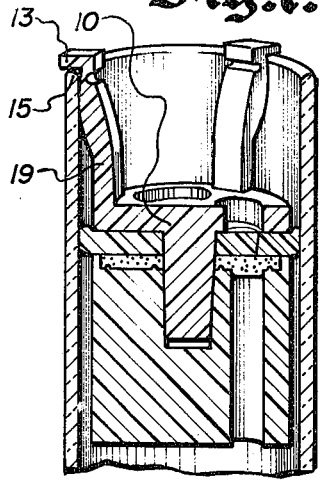
Figure 4:
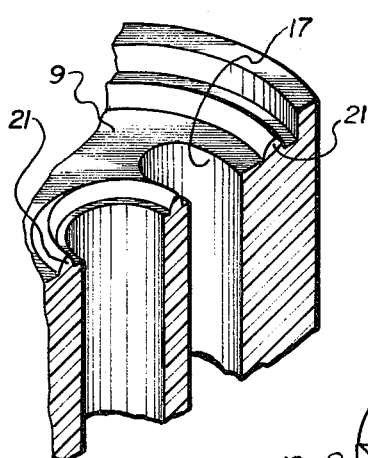
FIG. 4 is an enlarged fragmentary sectional view of a piston from the serum preparator, showing the detail of the sealing rings for preventing blowby between the piston and the filter.
Figure 5:
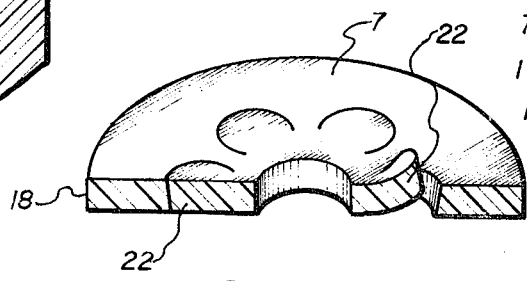
FIG. 5 is an enlarged sectional view of a barrier partition from the serum preparator, showing the detail of the slits serving as check valves.
Figure 9:
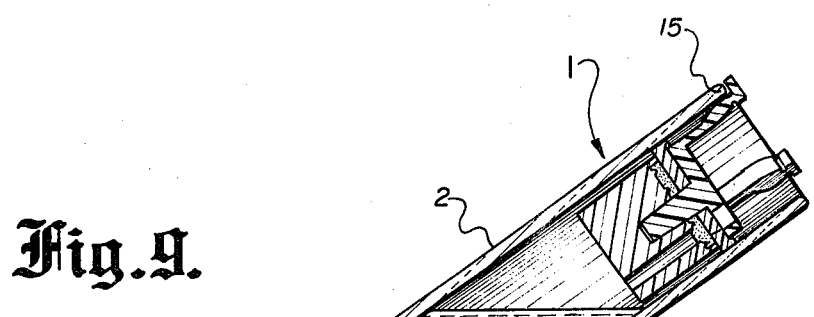
FIG. 9, FIG. 10, FIG. 11 and FIG. 12 are each a sectional view of the serum preparator and the centrifuge tube. Each of the FIG.'s 9, 10, 11 and 12 are identical in view but each illustrates a different stage in the practice of the invention.
Figure 10:
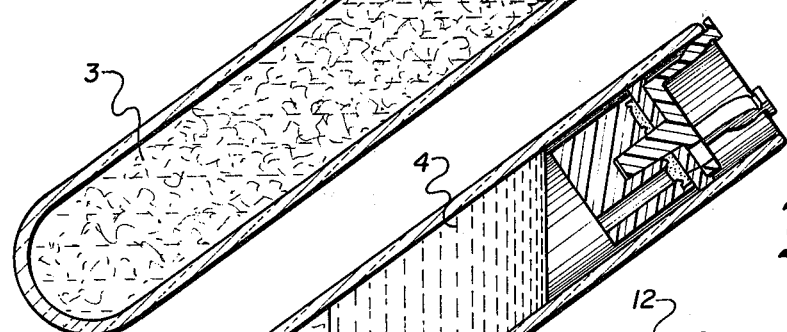
Figure 11:
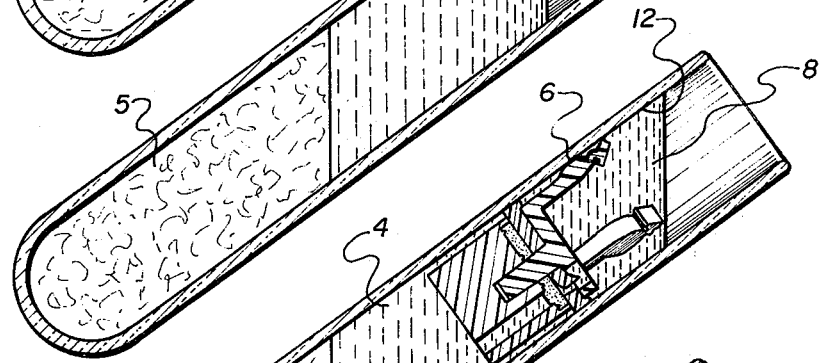
Figure 12:
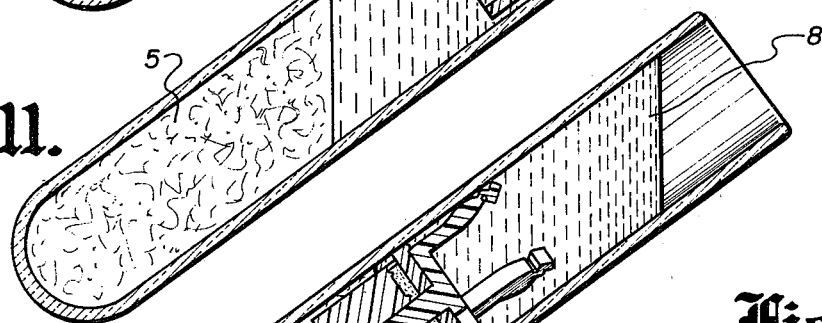
Figure 12:
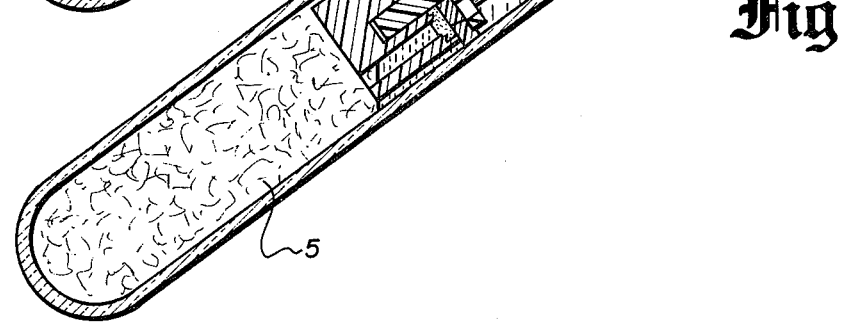

FIG. 1 illustrates a serum preparator (1) embodying the invention. FIG. 6 and FIG. 7 illustrate the insertion of the serum preparator (1) into a tube (2). The blood sample (3) is collected by the tube (2) prior to the insertion of the serum preparator (1). FIG. 9 illustrates the orientation of the tube (2) and the serum preparator (1) above the blood sample (3) as they are loaded into a centrifuge. FIG. 10 illustrates the first phase of centrifugation where the serum (4) separates from the cellular components (5) while the serum preparator (1) is held in check. FIG. 11 illustrates the second phase of centrifugation at a higher rotational speed, where the serum (4) has been completely clarified and the serum preparator (1) has been released from its check position by the increased centrifugal speed and is shown to be sedimenting down the bore of the tube (2), filtering fibrin and other particulates from the serum (4) as it sediments. The sedimentation velocity of the device is reduced by a brake (6). FIG. 12 illustrates where the serum preparator (1) is stopped by its isopycnic equilibrium astride the interface of the serum (4) and cellular (5) components. When the serum preparator (1) stops, it forms a partition (7) to protect the serum filtrate (8) from contamination by the unfiltered portion of the blood sample (3).

The essence of the invention is the inclusion of a combination of means for restraining the sedimentation of the piston (9) in order to exclude slowly sedimenting cellular components (5) from the serum filtrate (8), thereby to improve the quality of the filtrate (8). The failure of those skilled in the art to recognize the need for restraining means was a major obstacle to the development of the invention.

A generic claim acts as an umbrella to include all species of restraining means which may reasonably be applied to the serum preparator (1) and which are known by those skilled in the art. Specific species claimed include a detent (10), a frictional brake (6), a hydraulic brake, and combinations of these species. A combination of these species, as illustrated in the drawings, is the best mode of the invention. However, also included under the generic claim are all alternative restraining means known by those skilled in the art, e.g., the voil volume delay device described by Gresl (supra) and the valve delay device described by Ayres (supra).

The best mode includes a detent (10) which restrains the sedimentation of the serum preparator (1) during the first phase of centrifugation in order to separate the serum (4) from cellular components (5). FIG. 10 illustrates a detent (10) holding the serum preparator (1) in its check position during the first phase of centrifugation.

Without restraint, the serum preparator (1) would sediment with approximately the same velocity as the clot and would overtake the more slowly sedimenting uncoagulated cellular components (5). The overtaken cells would either clog and overload or blow by the filter (11). The overtaken cells can lyse if they are trapped and smeared between the serum preparator (1) and the tube wall (12).

The best mode also includes a brake (6) or combination of brakes which restrain the sedimentation velocity during the second phase of centrifugation. Brakes are included with the serum preparator (1) in order to control the rate of filtration, to prevent blowby around the filter (11), and to prevent serum preparator (1) from overshooting its isopycnic equilibrium stop position.

Restraint on the Initiation of Sedimentation of the Serum Preparator During the Separation Phase of Centrifugation During the separation phase of centrifugation, the serum preparator (1) is held in check by a detent (10). The detent (10) has a catch (13) which is attached to the piston (9) by an arm (14). During insertion, the catch (13) comes to rest on a support provided by the lip (15) of the tube or equivalent support and causes the piston (9) to stop at a catch position within the bore of the tube (2). The detent (10) supports the piston (9) at the catch position. The detent (10) holds the piston (9) in check at the catch position during the separation phase of centrifugation when the blood sample (3) is separated into the serous (4) and cellular (5) components. The rotational speed of the separation phase of centrifugation is chosen so as to be less than sufficient to force the detent (10) from its support on the lip (15) of the tube. The detent (10) delays the initiation of the descent of the piston (9) until the slowly sedimenting components (5) of blood have had adequate time to pellet.

Release is effected by the application of a triggering centrifugal force, typically caused by an increase in the rotational speed of centrifugation. The triggering centrifugal force causes the detent (10) to slide from its support on the lip (15) of the tube and causes the piston (9) to slide from its catch position. In one embodiment, the detent (10) is elastic such that the triggering centrifugal force causes it to bend sufficiently to release the serum preparator (1). In another embodiment, the detent (10) has a point of weakness (16) such that the triggering centrifugal force causes the detent (10) to exceed its elastic limit, thereby allowing the detent (10) to rotate from its position of support. Upon initiation of the filtration phase of centrifugation, the serum preparator (1) is released from its catch position and proceeds to sediment down the tube (2), affecting the filtration of the serum supernatant (4).

Restraint on the Sedimentation Velocity of the Serum Preparator During the Filtration Phase of Centrifugation During the filtration phase of centrifugation, the serum preparator (1) sediments through the separated serum (4) and filters the separated serum (4) in its path. The filtration removes fibrin and other particulates from the separated serum (4). FIG. 11 illustrates the filtration of the serum supernatant (4). The serum preparator (1) has been released by the triggering force causing the detent (10) from its support. The filter (11) is attached to the piston (9). During centrifugation, the piston (9) carries and guides the filter (11) down the bore of the tube (2) through the serum supernatant (4). As the filter (11) travels down the bore of the tube (2), serum (4) passes through the filter (11) causing fibrin and other slowly sedimenting particulates to be removed from the serum supernatant (4). The resulting serum filtrate (8) is then an object for clinical analysis.

The invention embodied by the serum preparator (1) includes provisions to prevent blow-by of unfiltered serum (4) around the serum preparator (1) and around the filter (11). The piston (9) contains one or more aperture (17) for the passage of displaced serum (4) during sedimentation. The filter (11) is fitted over this aperture (17) to force all passing serum (4) to cross the filter (11). The filter (11) seals with the piston (9) in order to prevent blowby around the filter (11). An annular seal (18) around the piston (9) makes a sealing contact with the tube wall (12) to prevent blowby around the piston (9) and to force displaced serum (4) to pass through the aperture (17).

During the separation phase of centrifugation, the sedimentation velocity of the serum preparator (1) is restrained by a brake (6) or combination of brakes. Braking the sedimentation velocity causes several effects. The braking means slows the sedimentation of the piston (9) so that the piston (9) overtakes fewer slowly sedimenting particulates, including slowly sedimenting uncoagulated cells. The braking means also reduces blow-by around the filter (11) by reducing the pressure difference across the piston (9) and the filter (11). At a reduced pressure, less serum (4) will escape filtration by passing around the piston (9) and filter (11). Braking the sedimentation velocity of the serum preparator (1) reduces the rate of filtration and thereby reduces the possibility of filter overload. Braking the sedimentation velocity of the serum preparator (1) reduces the momentum of the the device and prevents the momentum from causing the device to overshoot its isopycnic equilibrium position.

In the first embodiment of the braking means, a frictional brake (6) reduces the sedimentation velocity of the piston (9) by exerting a frictional drag between the serum preparator (1) and the wall (12) of the tube as the serum preparator (1) travels within the tube (2). To achieve the frictional drag, brake pads (6) and brake springs (19) are added to the assembly. The brake springs (19) are attached to the piston (9) and act on the brake pads (6) to exert a normal force against the wall (12) of the tube for setting the frictional drag.

Figure 8:
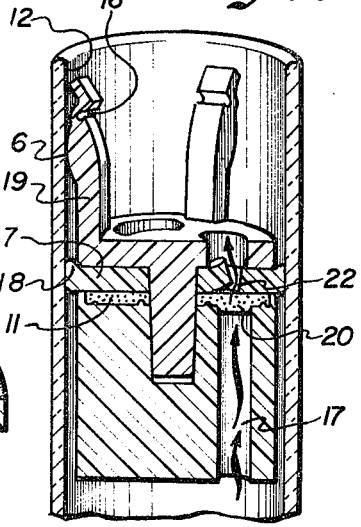
FIG. 8 is a sectional view of the serum preparator continued from FIG. 7, showing the serum preparator after it has been released by a triggering centrifugal force and has traveled down the bore of the tube.

In the second embodiment of the braking means, a hydraulic brake reduces the sedimentation velocity of the piston (9) by causing a resistive drag. The resistive drag is achieved by restricting the passage of displaced serum (4) across the piston (9) as the piston sediments. The serum preparator (1) includes an annular seal (18) around the piston (9) which forms a sealing contact with the wall (12) of the tube for preventing the passage of serum (4) between the piston (9) and the wall (12) of the tube. FIG. 6 and FIG. 8 illustrate the rim of the barrier partition (18) acting as the annular seal. The piston (9) provides one or more aperture (17) for the passage of serum (4) through the piston (9). The aperture (17) is the only means for passing serum (4) across the piston (9). Each aperture (17) includes a constriction for restricting and controlling the passage of displaced serum (4) through the piston (9), thereby braking the velocity of the piston (9). The constriction determines the resistive drag and the sedimentation velocity of the piston (9). The constriction may take different forms. The constriction may be integrally molded into the piston (9) orifice to restrict the flow of serum (4) through the piston (9) and the sedimentation velocity of the serum preparator (1).

The filter (11) can also serve as the constriction. The filter (20) can restrict the flow through the aperture (17). The filter (11) is sandwiched transversely in the piston (9) so as to span the aperture (17), forcing serum (4) passing through the apertures (17) to cross through the filter (20). Sealing rings (21) around the aperture (17), between the piston (9) and the sandwiched filter (11), prevent blow-by which could result from the large pressure difference which develops across the filter (20). The sealing rings (21) prevent the flow of serum (4) around the filter (11) and constrict the flow of the serum (4) to the portion of the filter (20) which spans the aperture (17).

Slits (22) in the barrier partition (7) can also serve as a constriction as well as serving as check valves. The slits (22) allow passage of serum across the barrier partition (7) in one direction only, viz. from the cellular side (5) to the serum filtrate side (8). Varying the size of the slits (22) varies the degree of constriction and determines the resistive drag of the hydraulic brake effect for the sedimentation velocity of the serum preparator (1).

Restraint on the Sedimentation Momentum of the Serum Preparator Approaching the Isopycnic Equilibrium Stop Position The serum preparator (1) is a density device which depends on its isopycnic density to stop its sedimentation at the interface of the separated serous (4) and cellular (5) components. The serum preparator (1) has an over all density which which is approximately isopycnic with the density of normal whole blood with a specific gravity between 1.01 and 1.09. The serum preparator (1) is more dense than normal serum (4) and less dense than a normal cellular pellet (5). The density of the serum preparator (1) allows it to sediment through serum (4) but causes it to be stopped by buoyant forces when partially submersed in the cellular pellet (5). The serum preparator (1) comes to rest at its point of isopycnic equilibrium, partially submersed in the cellular pellet (5) and partially overlaid by serum filtrate (8). At the isopycnic stop position, the centrifugal and buoyant forces on the serum preparator (1) are in balance. FIG. 12 illustrates the serum preparator (1) at its isopycnic equilibrium. The density of the serum preparator (1) and the location of the attachment of the filter (11) to the piston (9) is adapted so that the filter (11) remains within the serum component (4) at the isopycnic stop position.

The serum preparator (1) includes a brake means for damping its momentum as it approaches its isopycnic stop position. The momentum is dampened so that the serum preparator (1) will not overshoot the isopycnic stop position. Overshooting the isopycnic stop position can force cellular material (5) to pass the serum preparator (1) and to contaminate the serum filtrate (8). The brake means may include the frictional brake (6), the hydraulic brake or a combination of these brakes.

In order to desensitize the variation of the isopycnic stop position with variation in the density of the serum (4) and cellular (5) components from different individuals, one embodiment of the serum preparator (1) includes a displaced center of mass. The density composition of the serum preparator (1) is such that the center of mass is displaced from the center of volume toward the base of the serum preparator (1). The over all density, however, is still isopycnic. Displacing the center of mass causes the serum preparator (1) to display a narrower range of isopycnic stop positions for individuals having range of different densities of blood components. The best mode to displace the center of mass is to select a high density material for the detent (10) and a low density material for the piston (9). However, the overall density of the serum preparator (1) remains isopycnic.

Partition

The serum preparator (1) forms a partition (7) between the serum filtrate (8) and the unfiltered blood at the isopycnic stop position. The partition (7) isolates the serum filtrate (8) from contamination by the cellular pellet (5) during storage and decanting. The serum preparator (1) includes two species of barrier partition.

The first species of partition combines the piston (9), the annular seal (18), and the filter (20) to span the bore of the tube (2), to form a tight seal with the wall (12) of the tube, and to form a partition between the serum filtrate (8) and the unfiltered components (4&5). Using this species of partition, the user is able to decant or otherwise transfer the serum filtrate (8) without causing contamination by the flow of material from the cellular pellet (5).

The second species of the partition (7) includes a barrier partition (7) made of a material which is impermeable to the soluble components of blood. The piston (9) holds and orients the solute impermeable barrier partition (7). The solute impermeable barrier partition (7) has a check valve to allow the serum filtrate (8) to pass during the filtration phase. This species is useful for preventing contamination of the serum filtrate (8) both during decanting or transfer from the tube (2) and during storage and transport of the serum filtrate (8) within the tube (2).

I claim:

1. A serum preparator for enabling the separation of serum from blood, for filtering particulates from separated serum, and for partitioning serum filtrate from unfiltered blood, the blood contained within a tube adapted for centrifugation, the cellular components of blood sedimenting within the tube during centrifugation, thereby forming a cellular pellet and a supernatant of serum, the serum preparator comprising:

a piston adapted to be inserted into the open end of the tube and to sediment within the bore of the tube during centrifugation, and defining an aperture for the passage of serum through the piston during sedimentation, an annular seal between the piston and the tube for preventing blow-by of serum around the piston during sedimentation of the piston, thereby forcing displaced serum to pass through the aperture, a filter covering the aperture for filtering particulates from serum passing through the aperture, the filter sealed to the piston for preventing serum blow-by around the filter, and means for restraining the sedimentation of the piston during centifugation, the restraining means attached to the piston and contacting the tube for support, said restraining means holding and positioning the serum preparator at a catch position after insertion into the tube, said restraining means adapted to restrain the sedimentation of the serum preparator during centrifugation to enable the cellular components of blood to sediment sooner to the cellular pellet than the serum preparator, said restraining means including a detent attached to the piston and contacting the tube for positioning and holding the piston above the serum in the tube above the blood and for releasing the piston for travel down the bore of the tube, the release induced by the application a triggering force which forces the detent from its support position, the sedimentation of the piston within the tube causing passage of displaced serum through the aperture and across the filter, thereby filtering the serum, said serum preparator having a density approximately isopycnic with the density of blood, greater than the density of serum, and less than the density of the cellular pellet, thereby causing the serum preparator to have a stop position at isopycnic sedimentation equilibrium partially submersed in the cellular pellet and partially overlayed by the serum, said piston, annular seal, and filter acting in combination at the stop position to obstruct the passage of particulates across the serum preparator thereby partitioning the serum filtrate and the cellular pellet for preventing contamination of the serum filtate during storage and decanting.

2. A serum preparator as in claim 1 wherein the detent includes a resilient catch and an arm connecting the catch to the piston, the catch for resting on the support, the triggering force causing the release by the catch bending and sliding off the support by the application of the triggering force, the triggering force being an increased centrifugal force.

3. A serum preparator as in claim 1 wherein the detent includes a catch with a point of weakness and an arm connecting the catch to the piston, the catch for resting on the support, the triggering force causing the release by the catch rotating about the point of weakness and sliding off the support by the application of the triggering force, the triggering force being an increased centrifugal force.

4. A serum preparator as in claim 1 wherein the restraining means further includes means for braking the sedimentation velocity of the serum preparator, the braking means attached to the piston.

5. A serum preparator as in claim 1 further comprising a barrier partition impermeable to solutes and attached to and positioned by the piston for preventing diffusion of solutes between the cellular pellet and the serum filtrate across the serum preparator at the stop position.

6. A serum preparator as in claim 1 wherein the restraining means includes means for braking the sedimentation velocity of the serum preparator, the braking means attached to the piston.

7. A serum preparator as in claim 6 wherein the braking means includes one or more brake pads and one or more brake springs connecting the brake pads to the piston, the brake springs pressing the brake pads against the wall of the tube for creating frictional drag for slowing the sedimentation velocity of the serum preparator.

8. A serum preparator as in claim 6 further comprising a barrier partition impermeable to solutes and attached to and positioned by the piston for preventing diffusion of solutes between the cellular pellet and the serum filtrate across the serum preparator at the stop position.

9. A serum preparator as in claim 6 wherein the braking means includes a hydraulic brake.

10. A serum preparator as in claim 9 wherein the hydraulic brake includes a constriction of the aperture, for limiting the passage of displaced serum across the piston, thereby slowing the sedimentation velocity of the serum preparator.

11. A serum preparator as in claim 1 further comprising a barrier partition impermeable to solutes, attached to and held by the piston over the filter, having a check valve providing for passage of serum across the barrier partition during sedimentation, and forming a seal with the piston for preventing diffusion of solutes around and across the barrier partition at the stop position.

12. A serum preparator as in claim 11 wherein the restraining means includes:
a detent attached to the piston and contacting the support defined by the tube for positioning and holding the piston above the serum in the tube above the blood and for releasing the piston for travel down the bore of the tube, the release induced by the application of a triggering force which forces the detent from its support position,
means for braking the sedimentation velocity of the serum preparator, the braking means attached to the piston.

13. A serum preparator as in claim 12 wherein the check valve of the barrier partition is held sandwiched by the piston in a transverse position above the filter, the check valve open when the serum preparator is sedimenting for allowing the serum to flow through the aperture, the check valve closed at the stop position for partitioning the serum filtrate from the cellular pellet.

14. A serum preparator as in claim 1 wherein the center of mass of the serum preparator is displaced from the center of volume towards the centripetal end of the serum preparator, thereby decreasing the sensitivity of the sedimentation equilibrium point to changes in the density of blood, serum, and cellular pellet.

15. A method for separating serum from blood, for filtering the separated serum, and for partitioning the serum filtrate from unfiltered blood, the method using a tube for containing the blood and a serum preparator for filtering and partitioning the blood, the serum preparator having a density approximately isopycnic with blood and having,
a piston adapted to insert into the tube and to sediment within the tube and defining an aperture for the passage of serum,
an annular seal betweem the piston and the tube for preventing blow-by of serum around the piston during sedimentation and for forcing displaced serum to pass through the aperture,
a filter covering the aperture for filtering particulates from serum passing through the aperture, the filter sealed to the piston for preventing serum blow-by around the filter, and
a means for restraining the sedimentation of the piston, the restraining means attached to the piston, and including a detent attached to the piston and contacting the tube for positioning and holding the piston above the serum in the tube above the blood and for releasing the piston for travel down the bore of the tube, the piston, annular seal, and filter acting in combination to obstruct the passage of particulates across the serum preparator, the method comprising steps for, inserting the serum preparator into the tube containing the blood, for loading the assembled tube and serum preparator into a centrifuge rotor, for first spinning the loaded assembly in the rotor at a first speed sufficient to separate the serum and cellular components of blood and less than sufficient to overpower the restraining means so as to restrain the sedimentation of the serum preparator and to enable the cellular components of blood to sediment sooner to the cellular pellet than the serum preparator, and for second spinning the loaded assembly in the rotor at a second speed sufficient to overcome the restraining means so as to enable the serum preparator to sediment within the tube and to cause displaced serum to pass through the aperture and across the filter, thereby filtering the separated serum, said second spinning continued until the serum preparator has reached a stop position and established a partition thereat, said inserting of the serum preparator into the tube establishing a contact between the restraining means and the tube, thereby causing the serum preparator to be held at a catch position within the tube, said second spinning continuing until the sedimentation of the serum preparator effectively reaches the stop position at isopycnic equilibrium near the interface between the separated serum and the cellular pellet and establishes a partition thereat for preventing contamination of the serum filtrate by the cellular pellet during storage and decanting.

16. A method as in claim 15 wherein the second speed of said second spinning is sufficient to overcome the contact between the tube and the restraining means so as to enable the serum preparator to escape its catch position and to sediment within the tube, but the second speed is not so excessive as to cause the restraining means to fail to restrain the velocity of the sedimentation of the serum preparator so as to allow filter overload or blowby.

* * * * *